United States Patent
Miller et al.

(10) Patent No.: US 7,125,580 B2
(45) Date of Patent: Oct. 24, 2006

(54) METHOD FOR PREPARING A SOLID PHASE MICROEXTRACTION DEVICE USING AEROGEL

(75) Inventors: Fred S. Miller, Bethel Island, CA (US); Brian D. Andresen, Livermore, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 11/146,562

(22) Filed: Jun. 6, 2005

(65) Prior Publication Data

US 2005/0233085 A1  Oct. 20, 2005

Related U.S. Application Data

(62) Division of application No. 09/394,159, filed on Sep. 13, 1999, now Pat. No. 6,905,031.

(51) Int. Cl.
*B05D 1/00* (2006.01)
*B05D 1/02* (2006.01)

(52) U.S. Cl. .............. 427/202; 427/443.2; 427/427; 427/427.4

(58) Field of Classification Search ........... 427/202, 427/443.2, 427, 427.4
See application file for complete search history.

(56) References Cited

U.S. PATENT DOCUMENTS

| | | | | |
|---|---|---|---|---|
| 4,335,017 A * | 6/1982 | Miles et al. | ............ | 502/7 |
| 4,650,784 A | 3/1987 | Ramsden et al. | ............ | 502/407 |
| 4,680,121 A | 7/1987 | Ramsden et al. | ............ | 210/635 |
| 5,066,395 A | 11/1991 | Ramsden et al. | ............ | 210/198.2 |
| 5,087,359 A | 2/1992 | Kakodkar et al. | ............ | 210/198.2 |
| 5,137,626 A | 8/1992 | Parry et al. | ............ | 210/198.2 |
| 5,470,612 A * | 11/1995 | Hotaling et al. | ............ | 427/377 |
| 5,496,741 A | 3/1996 | Pawliszyn | ............ | 436/163 |
| 5,576,217 A | 11/1996 | Hsu | ............ | 436/126 |
| 5,639,372 A | 6/1997 | Hagen et al. | ............ | 210/635 |
| 5,691,206 A | 11/1997 | Pawliszyn | ............ | 436/178 |
| 5,693,228 A | 12/1997 | Koehler et al. | ............ | 210/656 |
| 5,702,610 A | 12/1997 | Hagen et al. | ............ | 210/670 |
| 5,738,790 A | 4/1998 | Hagen et al. | ............ | 210/635 |
| 5,759,939 A | 6/1998 | Klabunde et al. | ............ | 502/328 |
| 5,859,362 A | 1/1999 | Neudorfl et al. | ............ | 73/23.2 |
| 5,869,141 A * | 2/1999 | Blohowiak et al. | ............ | 427/309 |
| 5,891,559 A | 4/1999 | Goken et al. | ............ | 428/220 |
| 5,911,883 A | 6/1999 | Anderson | ............ | 210/679 |

\* cited by examiner

*Primary Examiner*—Fred J. Parker
(74) *Attorney, Agent, or Firm*—Alan H. Thompson

(57) ABSTRACT

A sample collection substrate of aerogel and/or xerogel materials bound to a support structure is used as a solid phase microextraction (SPME) device. The xerogels and aerogels may be organic or inorganic and doped with metals or other compounds to target specific chemical analytes. The support structure is typically formed of a glass fiber or a metal wire (stainless steel or kovar). The devices are made by applying gel solution to the support structures and drying the solution to form aerogel or xerogel. Aerogel particles may be attached to the wet layer before drying to increase sample collection surface area. These devices are robust, stable in fields of high radiation, and highly effective at collecting gas and liquid samples while maintaining superior mechanical and thermal stability during routine use. Aerogel SPME devices are advantageous for use in GC/MS analyses due to their lack of interfering background and tolerance of GC thermal cycling.

7 Claims, 2 Drawing Sheets

METHOD FOR PREPARING A SOLID PHASE MICROEXTRACTION DEVICE USING AEROGEL

RELATED APPLICATIONS

This application is being filed as a Divisional application of application Ser. No. 09/394,159 filed Sep. 13, 1999, now U.S. Pat. No. 6,905,031, entitled "Solid Phase Microextraction Device Using Aerogel" and incorporated herein by reference.

The United States Government has rights in this invention pursuant to Contract No. W-7405-ENG-48 between the United States Department of Energy and the University of California for the operation of Lawrence Livermore National Laboratory.

BACKGROUND OF THE INVENTION

1. Field of the Invention

This invention relates to xerogel and aerogel substrates as sample collection media, and more particularly to a solid phase microextraction device using these substrates.

2. Description of Related Art

Solid Phase Microextraction (SPME) is an analytical chemical isolation technique to extract trace compounds from the air or liquid samples with high efficiency. The extraction device typically uses fused silica (glass) fibers coated with an absorbing polymer (e.g., siloxanes, silanes, silicone). Glass is used to match the thermal expansion of the fiber coating under extreme temperature conditions. The coated glass fiber is capable of extracting organic and organo-metallic compounds from the air and liquid samples. Currently, the coated glass fiber (~1 cm long) is glued to a metal wire (~300 $\mu$m) supported inside a hollow needle that can be inserted into the hot injection port of a gas chromatograph (GC) or GC mass spectrometer (GC-MS). U.S. Pat. No. 5,691,206 to Pawliszyn describes a method and device for carrying out solid phase microextraction.

This conventional technique is problematic because the glass fiber tip is fragile and can be easily broken off when used in the field or laboratory. The polymer coating has a limited lifetime and can peel away following repeated collections and analyses under the high thermal cycle stress at the GC injection port or after exposure to high field radiation. The manufacturing of the SPME assembly also requires the time-consuming process of gluing the glass fiber to the wire support. The engineering difficulties encountered in the current glass fiber design result in a high cost per unit.

Another disadvantage of the current SPME techniques is the time required extracting the sample by the coated fibers. U.S. Pat. No. 5,693,228 to Koehler et al. provides a device that vibrates the fiber during extraction to shorten adsorption time. However, this approach requires additional hardware incorporated into the conventional SPME syringe.

A need exists for an improved SPME assembly that addresses the deficiencies of the prior art. The present invention circumvents the above-mentioned problems and provides a more robust, highly selective, rapidly adsorbing SPME assembly that effectively extracts samples from gas or liquid samples.

SUMMARY OF THE INVENTION

An object of the present invention is to provide a solid phase microextraction (SPME) device using aerogel and xerogel materials coated on a support structure, such as a stainless steel or kovar wire or glass fiber. It is further an object to provide a device that can be manufactured easily and quickly absorb or adsorb sample fluids—i.e., gases and liquids. Another object is to provide a sample collection medium using aerogel and/or xerogel materials to absorb either a wide range of analytes or selectively target specific analytes; this selectivity can be accomplished by alteration of the sol-gel chemistry and processing techniques used to make the aerogels and xerogels. The present SPME device is robust and formed of materials that are commercially available, inexpensive, and stable under high field radiation and high thermal stress. The aerogel SPME device can easily tolerate the thermal cycling conditions in GC/MS without peeling or releasing interfering compounds.

The invention basically involves a SPME collection assembly comprising a support structure coated with organic and/or inorganic aerogels, xerogels, or combinations thereof. The support structure may be formed of stainless steel or kovar wire or a glass or high temperature plastic fiber. The stainless steel and kovar wire supports can be advantageous with silica substrates because their thermal expansion rates are comparable to glass. The aerogel and xerogel materials have extremely high porosity and surface area to absorb the targeted analytes and can be applied in various forms, including thin films and small particles. Inorganic and organic aerogels and xerogels can be doped with various metals and compounds to selectively adsorb specific analytes and confer other beneficial properties.

The support structure can be coated with the sample collection substrate by dipping the fiber or wire in a sol-gel solution and then drying the material to form a film or coating. The drying process determines whether the material is an aerogel or xerogel. Before the initial coating is completely dried, small particles of aerogel may be applied to the wet coating and thereby cemented to the support structure to increase the sample collection surface area.

U.S. Pat. Nos. 5,275,796, 5,409,683, and 5,686,031 describe the formation of aerogels and xerogels using sol-gel chemistry in which a precursor solution is gelled and then dried by removing the liquid from a two-phase liquid-solid network. Ultralightweight materials, called aerogels, are typically dried by extracting the liquid under supercritical conditions. Denser materials, called xerogels, are formed by evaporating the liquid under ambient conditions, which causes significant shrinkage of the solid network. In evaporative drying, the surface tension of the liquid in the small pores creates extremely high forces as the material dries, which tends to collapse the weak solid structure of the gel. The gels are typically not strong enough to resist this shrinkage during evaporation.

The present invention is useful in collecting airborne and liquid samples for environmental monitoring (e.g., pollutants), drug and contraband detection, and military applications (e.g., chemical and biological weapons detection and monitoring). The invention can be used to detect trace and ultratrace amounts (e.g., ppb, ppt levels) of volatile and semivolatile organic analytes such as pesticides, herbicides, polychlorinated biphenyl compounds (PCBs), and polynuclear aromatic hydrocarbon compounds (PAHs).

Other objects, features, and advantages of the present invention will become apparent from the following description and accompanying drawings.

BRIEF DESCRIPTION OF THE DRAWINGS

The accompanying drawings, which are incorporated into and form part of this disclosure, illustrate embodiments of the invention and together with the description, serve to explain the principles of the invention.

DETAILED DESCRIPTION OF THE INVENTION

The present invention is a solid phase microextraction (SPME) device or assembly using a support structure coated with a substrate formed of aerogel, xerogel, or combinations thereof. The xerogels and aerogels may be organic (i.e., carbon-based) or made from a variety of metal oxides (e.g., silica, tantala, zirconia). The gel solution can be doped with various metals or other compounds, thereby incorporating them into the solid network or lattice of the substrate material. The support structure may be formed of glass fiber, a high temperature plastic, or a metal wire such as stainless steel or kovar. Kovar wire is index-matched to the thermal expansion of glass, which is advantageous when using silica-based xerogel and aerogel coating materials. Stainless steel also has a thermal expansion similar to glass and is more robust than kovar.

This invention allows many different types of SPME collection fibers to be designed that are tailored to specific collection schemes and to target certain chemical analytes. The SPME device according to the present invention is robust, stable in fields of high radiation, and capable of efficiently collecting the target species in the environment while maintaining superior mechanical and thermal stability during routine use. The aerogel/xerogel collection device is easier to manufacture than conventional silica fibers and can be made of any size and length for specific collection scenarios.

Figure 1:
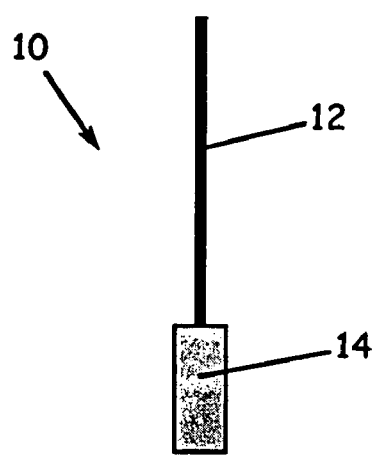
FIG. 1 shows a SPME device according to the present invention.

FIG. 1 shows a SPME collection device 10 according to the present invention. In this embodiment, a support structure 12 made of thin metal wire (e.g., 200–250 micron) is coated with a sample collection substrate 14 made of xerogel, aerogel, or a combination thereof, collectively referred to hereafter as "aerogel". The substrate is formed of an inorganic and/or organic aerogel that may contain or be doped with one or more metals. A greater number of compounds can be collected with the aerogel SPME assembly than conventional systems, as the aerogel material can be specially designed to absorb a wide range of analytes or alternatively for specific analytes.

The wire support structure 12 is made of stainless steel or kovar, which is a group of alloys containing iron, nickel, cobalt, and manganese characterized by a low coefficient of expansion. The expansivity of kovar is similar to that of glass, and thus it is used in making metal-to-glass seals. The alloys are useful in applications where a temperature variation can be expected. A representative alloy composition is Fe 53.8%, Ni 29%, Co 17%, Mn 0.2%. Glass or high temperature plastic fiber can be substituted for the wire, but the use of stainless steel wire provides a more robust SPME assembly and wider field collection applications. To improve the adherence or bonding of the aerogel substrate 14 on the support structure 12 (or to reduce its diameter), the wire or glass fiber support structure may be etched with acid.

The composition of the aerogel collection material is bound by specific requirements. The collection medium must be capable of selectively absorbing or adsorbing an analytically sufficient amount of a selected analyte or analytes within a reasonable period of time and then retaining the analytes until analysis. For use in direct GC/MS analysis, the collection material must absorb the analytes and then release them when heated in the GC/MS port. The aerogel substrate should not destroy or bind the analyte so that it cannot be released for analysis. The analyte is retained by the aerogel substrate by some form of chemical attraction; however, the substrate should not chemically convert the analyte (e.g., through catalysis) to another compound that will not accurately reflect the concentration of the analyte.

The collection medium must be capable of withstanding the GC/MS thermal release process without itself releasing species that would create an interfering spectrum. Aerogel has no negative effects from GC/MS thermal cycling on its release of absorbed constituents, so its thermal life is much greater than commercially available polymers. The thermal cycling can condition the aerogel tip and optimize the adsorption profile. Even if thermal expansion cracks the aerogel coating, the substrate is attached so securely to the wire or fiber that it does not peel or flake off. Aerogel has virtually no background signal for the GC/MS, unlike other polymeric tip coatings whose background signal can interfere with the detected compounds. The aerogel collection substrate is reusable: after the sample is desorbed in the GC/MS, the device can be used again to collect another sample. Alternatively, the SPME devices may be disposable due to the relatively low cost of materials and manufacturing.

The aerogel substrate may be designed to absorb a wide range of analytes, or a specific analyte or class of analytes. The ability to design both types of tips with a collection substrate that tolerates thermal cycling is advantageous. The requirement of chemical selectivity is important in certain applications, given the high sensitivity now obtained by analytical instrumentation, which may precludes the use of an arbitrary collection system (e.g., activated charcoal). Too many compounds in the collection medium can interfere with each other, requiring timely extractions and chemical separations to isolate the specific analyte of interest. Selectivity in certain applications thus simplifies and hastens the analyses.

Xerogels and aerogels are uniquely qualified for extraction of samples due to their high surface area, high porosity, and open-cell microstructure. The time required to extract a sample may therefore be improved as a highly porous material has quicker uptake of analyte. The aerogel materials are prepared by sol-gel reactions and processed by drying the gel under various conditions. If the gel is dried under supercritical conditions, the gel avoids collapse of the cell structure due to surface tension. The microstructure of the aerogel resembles a three-dimensional network of interconnected beads of about 10–100 Å in size, with pore diameters formed by the bead structure of about 50–500 Å. The basic synthetic approach to create inorganic aerogels is the co-hydrolysis and condensation of a metal alkoxide with the matrix alkoxide. Metal oxide aerogels commonly include silica, titania, tantala, vanadia, zirconia, hafnia, niobia, and alumina.

A wide variety of aerogels can be formed by methods described in the literature, including U.S. Pat. Nos. 5,275,796, 5,409,683, 5,686,031, and 5,395,805, all of which are hereby incorporated by reference. U.S. Pat. No. 5,851,947 to Hair et al. discusses the incorporation of noble metals into aerogels and is hereby incorporated by reference. Organic (carbon) aerogels are also well described in the literature, including U.S. Pat. Nos. 4,873,218, 4,997,804, 5,0811,63, 5,086,085, 5,420,168, 5,508,341, 5,476,878, 5,556,892, 5,908,896, and 5,744,510, all of which are hereby incorporated by reference. The manufacturing processes and composition of the aerogels can be varied to modify the chemical, physical, and optical properties, including density, clarity (or opacity), index of refraction, surface area, pore size, and porosity.

The composition of aerogels is highly variable. Virtually any metal (transition metals, rare earths, alkaline earths, alkali metals) or combination of metals can be incorporated into aerogels: Fe, Co, Ni, Cr, Cu, Mo, Ta, W, Ru, Rh, Pd, Os, Ir, Pt, Cd, Ce, Pr, Au, Hg, Ag, Zn, Zr, Ti, Hf, Ni, Al, V, Mn, Sc, Mg, Na, K, Ca, Sr, and Ba. Metal salts are also used, such as silver fluoride, silver nitrate, nickel nitrate, copper nitrate, iron nitrate, cobalt sulfate. The selection of metal(s) incorporated into the aerogel matrix is determined by which specific compounds of interest are to be adsorbed.

Figure 2A:
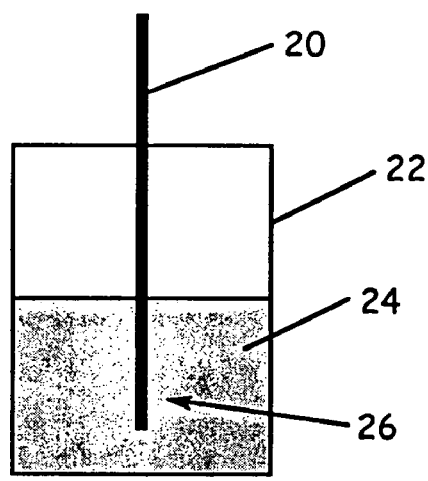
FIG. 2 shows a process for manufacturing SPME devices according to the present invention.
Figure 2B:
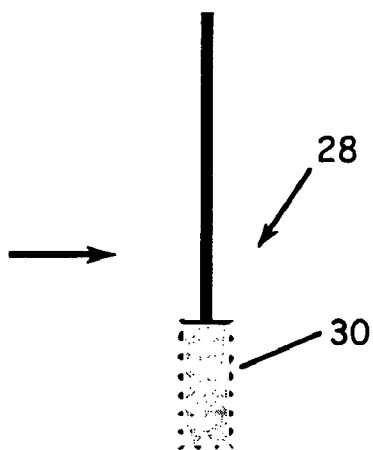

Another important feature of aerogel materials is that they can be made in a variety of forms: powders, films, fibers, microspheres, sheets, or monoliths of any size. In the present invention, the preferred approach is to form a thin film or a layer of microspheres of aerogel or xerogel on the end of the support structure. FIGS. 2A–2B show an example of the manufacturing process for an aerogel SPME device. The support structure 20 is placed or suspended in a container 22 with the aerogel precursor solution 24 to coat the end 26 of the structure 20. The coated fiber or wire 28 is then removed from solution and dried. The coated wire 28 may be dried in another vessel, or excess solution drained from the original container 22. The substrate layer or coating is dried either by evaporation to form a xerogel SPME device, or by a drying procedure that forms an aerogel SPME device, such as supercritical extraction in a pressurized vessel. A post-treatment heating of the aerogel device may improve the adsorptive properties. The support structure can be coated one or more times with gel precursor solution, and may be coated using techniques other than dipping, such as rolling or spraying.

Monoliths of aerogel material can be manufactured and then ground into smaller particles, which are then used to coat the end of the support structure. A thin film of aerogel solution may be applied to the tip as described above, and then the tip is rolled in, dipped in, or sprayed with small aerogel particles 30 so as to adhere to the wet coating. As the film dries, the aerogel particles are "cemented" to the thin film, which may be a xerogel. The aerogel particles may be homogeneous or have a variety of sizes and compositions (e.g., a mixture of metal oxide aerogels and carbon aerogels). The use of a microsphere coating or a coating of ground particles is advantageous since the collective surface area of the spheres (e.g., 200–600 Å diameter) is greater than a thin film, exposing active absorbent sites that aid in sample collection. The surface areas for aerogels are highly variable; silica aerogels, for example, typically range from 300–1200 $m^2/g$.

Figure 3:
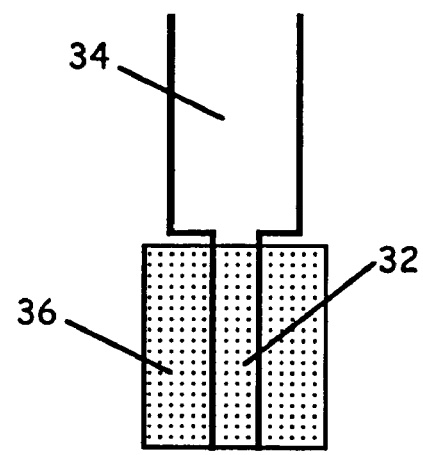
FIG. 3 shows a SPME device according to the present invention.

The coated end 32 of the support structure 34 may be tapered or have a smaller diameter or thickness, as shown in FIG. 3, to provide for a thicker layer 36 of aerogel without greatly increasing the diameter at the end. A support structure made of high temperature plastic may be molded to form such a shape. The original diameter of the support structure 34 (e.g., glass or wire) may be reduced by etching with acid before applying the substrate layer. The outer diameter of the support structure with the aerogel coating is limited by the interior diameter (bore size) of the hollow needle (described below) in which the SPME device is mounted.

Figure 4:
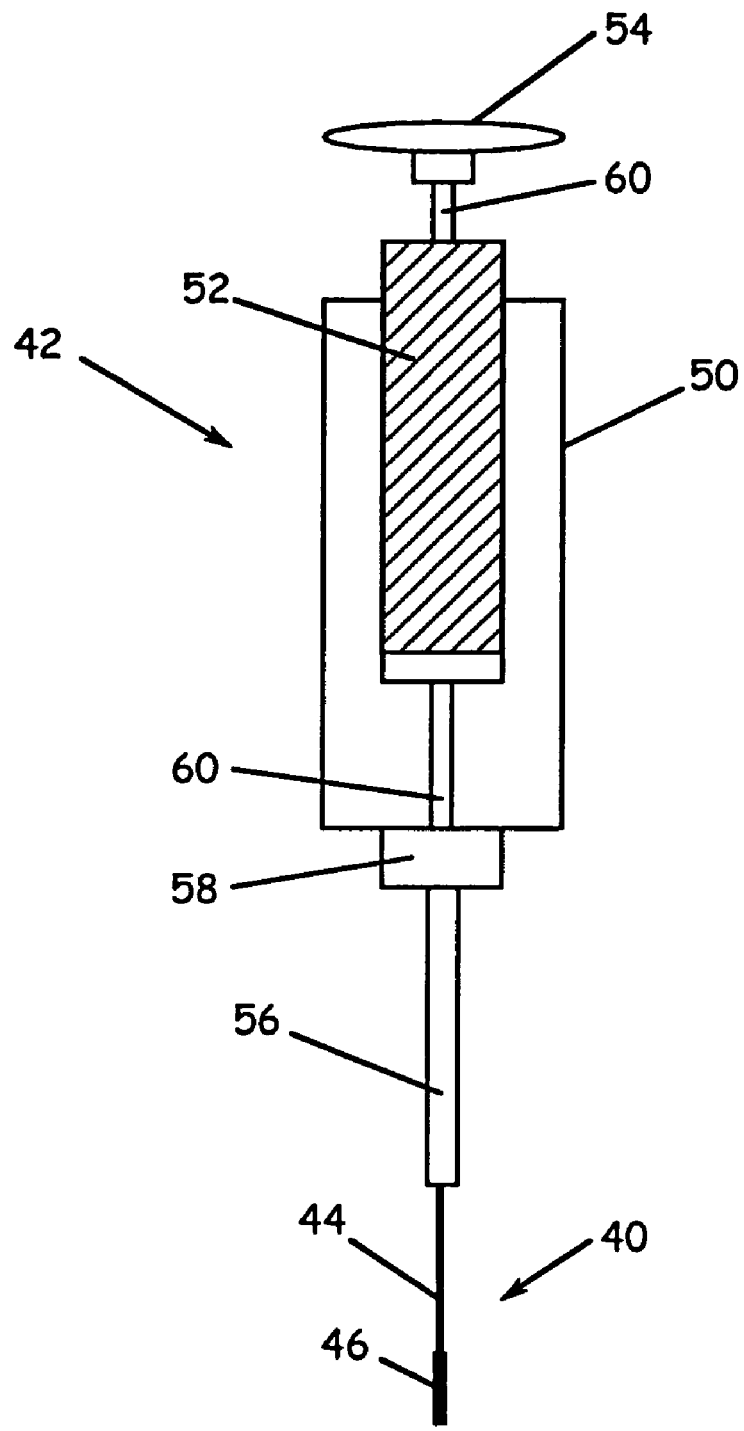
FIG. 4 shows a SPME device in a syringe.

FIG. 4 shows a SPME device 40 according to the present invention in a syringe 42 for carrying out solid phase microextraction with GC/MS. The SPME device 40 is a support structure 44 with an aerogel collection substrate 46 at the end. The device 40 is contained in a syringe 42, which has a barrel 50 and slidable plunger 52 that extends from one end of the barrel 50. The plunger 52 has a handle 54 at the top. A hollow needle 56 extends from the other end of the barrel 50 opposite the plunger 52. The needle 56 is connected to the barrel 50 by a connector 58.

The SPME device 40 is mounted to the top of the plunger 52 and may be enclosed in a metal sleeve 60 to protect the device 40 from damage. The device 40 extends through the plunger 52 and the needle 56 and moves longitudinally as the plunger 52 slides within the barrel 50. When the plunger 52 is depressed, the coated end of the device 40 extends beyond the end of the needle 56, as shown. When the plunger 52 is withdrawn, the device 40 is retracted within the needle 56 to protect the device 40 from damage.

To collect a sample, the needle 56 is typically inserted through a septum or membrane into a sample reservoir (e.g., a vial). The plunger 52 is depressed, exposing the device 40 to the sample. The aerogel coating 46 acts as an adsorbent to extract a sample. The tip is retracted after sample collection, and the needle 56 is withdrawn. To load the sample on a gas chromatograph for analysis, the needle 56 is inserted through the septum of the GC injection port and the device 40 is extended. While in the injector, the sample analytes are thermally desorbed from the aerogel substrate 46 and transferred to the GC column for analysis. U.S. Pat. No. 5,691, 206 to Pawliszyn describes a method and device for carrying out solid phase microextraction and is hereby incorporated by reference.

Aerogel substrates were fabricated and tested. The substrates absorbed a variety of liquid and gaseous organic and inorganic compounds, including iodine vapor, acetonitrile, benzene, butyl ether, carbon tetrachloride, 1-chloropropane, diethylamine, diisopropylamine, 2(diisopropyl)amino ethanol, diisopropylmethyl phosphate, dodecane, ethyl dichlorophosphate, diethyl chlorothiophosphate, 2-hexanone, iodobenzene, methyl chloroform, methyl iodide, 4-methyl-2-pentanone, nitrobenzene, nitromethane, 1-thiopropane, 2,2,-thiodiethanol, trimethyl phosphate, tributyl phosphate, kerosene, and m-xylene.

Silica aerogels with silver and silver/copper were effective with chloro compounds. Vanadium aerogels were effective with phosphate compounds. Many types of aerogel materials absorbed dodecane, including silica aerogels with copper, cobalt III, platinum IV, nickel, iron, sodium palladium, and niobium/nickel/cadmium. Cobalt and silver aerogels detected iodine compounds. Mixtures of organic and inorganic aerogels have proven successful for a wide variety of analytes; an illustrative example is a mixture of equal parts (¼) of carbon aerogel and aerogels doped (2–3%) with titanium, magnesium, and iron, respectively.

The foregoing description of preferred embodiments of the invention is presented for purposes of illustration and description and is not intended to be exhaustive or to limit the invention to the precise form disclosed. Many modifications and variations are possible in light of the above teaching. The embodiments were chosen and described to best explain the principles of the invention and its practical application to thereby enable others skilled in the art to best use the invention in various embodiments and with various modifications suited to the particular use contemplated.

The invention claimed is:

1. A method for forming a solid phase microextraction apparatus, comprising:

applying a layer of a gel precursor solution on at least the end of a support structure formed of a material selected from the group consisting of glass fibers, plastic fibers, and a metal wire, wherein the layer covers the entire perimeter of one end of the support structure;

drying the layer to form a sample collection substrate, wherein the substrate comprises a material selected from the group consisting of organic aerogels, inorganic aerogels, inorganic xerogels, organic xerogels, and combinations thereof; and applying particles on the layer before drying the layer, wherein the particles comprise a material selected from the group consisting of organic aerogels, organic xerogels, inorganic aerogels, inorganic xerogels, and combinations thereof.

2. The method as recited in claim 1, wherein drying the layer is selected from the group consisting of evaporative drying and supercritical extraction.

3. The method as recited in claim 1, further comprising applying a plurality of layers of the gel precursor solution.

4. The method as recited in claim 1, wherein applying the layer is carried out by a method selected from the group consisting of dipping, rolling, and spraying.

5. The method as recited in claim 1, wherein the layer comprises xerogel and further comprising applying particles of aerogel on the layer before drying the layer.

6. The method as recited in claim 1, further comprising etching at least the end of the support structure before applying the layer.

7. The method as recited in claim 1, further comprising heating the sample collection substrate on the support structure after drying to condition the substrate.

* * * * *